United States Patent
Koyrakh et al.

(10) Patent No.: US 10,362,963 B2
(45) Date of Patent: Jul. 30, 2019

(54) CORRECTION OF SHIFT AND DRIFT IN IMPEDANCE-BASED MEDICAL DEVICE NAVIGATION USING MAGNETIC FIELD INFORMATION

(75) Inventors: Lev A. Koyrakh, Plymouth, MN (US); Vasily Vylkov, Blaine, MN (US); Eric S. Olson, Maplewood, MN (US)

(73) Assignee: ST. JUDE MEDICAL, ATRIAL FIBRILLATION DIVISION, INC., St. Paul, MN (US)

( * ) Notice: Subject to any disclaimer, the term of this patent is extended or adjusted under 35 U.S.C. 154(b) by 160 days.

(21) Appl. No.: 13/584,197

(22) Filed: Aug. 13, 2012

(65) Prior Publication Data

US 2012/0302869 A1 Nov. 29, 2012

Related U.S. Application Data

(63) Continuation-in-part of application No. 13/087,203, filed on Apr. 14, 2011, now Pat. No. 9,901,303, and
(Continued)

(51) Int. Cl.
*A61B 5/05* (2006.01)
*A61B 5/06* (2006.01)
(Continued)

(52) U.S. Cl.
CPC ............. *A61B 5/062* (2013.01); *A61B 5/065* (2013.01); *A61B 34/20* (2016.02);
(Continued)

(58) Field of Classification Search
USPC ........................................................ 600/424
See application file for complete search history.

(56) References Cited

U.S. PATENT DOCUMENTS 5,297,549 A 3/1994 Beatty et al.
5,391,199 A 2/1995 Ben-Haim
(Continued)

FOREIGN PATENT DOCUMENTS

CN 101782358 7/2010
CN 103298516 9/2013
(Continued)

OTHER PUBLICATIONS

International Search Report and Written Opinion issued in International (PCT) Patent Application No. PCT/US08/054969 (dated Aug. 15, 2008).
(Continued)

*Primary Examiner* — Jonathan Cwern
(74) *Attorney, Agent, or Firm* — Dykema Gossett PLLC

(57) ABSTRACT

A system and method for navigating a medical device within a body are provided. The system includes an electronic control unit configured to determine operating positions for electrical and magnetic position sensors on the medical device within corresponding first and second coordinate systems. The first and second coordinate systems are defined by an electric field based positioning system and a magnetic field based positioning system, respectively. The magnetic position sensor is disposed proximate the electrical position sensor. The ECU is further configured to apply a mapping function correlating the operating positions which generates a mapped position for the magnetic position sensor in the first coordinate system responsive to the operating position of the magnetic position sensor in the second coordinate system. The ECU determines an adjusted operating position for the electrical position sensor in the first coordinate system responsive to the mapped position of the magnetic position sensor.

20 Claims, 6 Drawing Sheets

Related U.S. Application Data a continuation-in-part of application No. 13/231,284, filed on Sep. 13, 2011.

(51) Int. Cl.
  *A61B 34/20* (2016.01)
  *A61B 90/00* (2016.01)

(52) U.S. Cl.
  CPC .............. *A61B 2034/2051* (2016.02); *A61B 2034/2053* (2016.02); *A61B 2090/0818* (2016.02)

(56) References Cited

U.S. PATENT DOCUMENTS

| | | | |
|---|---|---|---|
| 5,480,422 A | 1/1996 | Ben-Haim | |
| 5,546,951 A | 8/1996 | Ben-Haim | |
| 5,568,809 A | 10/1996 | Ben-Haim | |
| 5,662,108 A | 9/1997 | Budd et al. | |
| 5,694,945 A | 12/1997 | Ben-Haim | |
| 5,697,337 A | 12/1997 | Takahashi et al. | |
| 5,697,377 A | 12/1997 | Wittkampf | |
| 5,718,241 A | 2/1998 | Ben-Haim et al. | |
| 5,738,096 A | 4/1998 | Ben-Haim | |
| 5,840,025 A | 11/1998 | Ben-Haim | |
| 5,944,022 A | 8/1999 | Nardella et al. | |
| 5,954,665 A | 9/1999 | Ben-Haim | |
| 5,983,126 A | 11/1999 | Wittkampf | |
| 6,016,439 A | 1/2000 | Acker | |
| 6,063,022 A * | 5/2000 | Ben-Haim | A61N 1/06 600/41 |
| 6,066,094 A | 5/2000 | Ben-Haim | |
| 6,226,542 B1 | 5/2001 | Reisfeld | |
| 6,233,476 B1 | 5/2001 | Strommer | |
| 6,288,785 B1 | 9/2001 | Frantz | |
| 6,301,496 B1 * | 10/2001 | Reisfeld | A61B 5/04011 345/419 |
| 6,640,119 B1 | 10/2003 | Budd et al. | |
| 6,728,562 B1 | 4/2004 | Budd et al. | |
| 6,939,309 B1 | 9/2005 | Beatty et al. | |
| 6,947,785 B1 | 9/2005 | Beatty et al. | |
| 6,978,168 B2 | 12/2005 | Beatty et al. | |
| 6,990,370 B1 | 1/2006 | Beatty et al. | |
| 7,072,707 B2 | 7/2006 | Galloway | |
| 7,088,099 B2 | 8/2006 | Doddrell | |
| 7,187,810 B2 | 3/2007 | Clune et al. | |
| 7,197,354 B2 | 3/2007 | Sobe | |
| 7,263,397 B2 | 8/2007 | Hauck | |
| 7,379,769 B2 | 5/2008 | Piron | |
| 7,386,339 B2 | 6/2008 | Strommer | |
| 7,536,218 B2 | 5/2009 | Govari | |
| 7,583,275 B2 | 9/2009 | Neumann | |
| 7,672,504 B2 | 3/2010 | Childers et al. | |
| 7,747,305 B2 | 6/2010 | Dean | |
| 8,111,059 B1 * | 2/2012 | King et al. | 324/117 R |
| 8,326,419 B2 | 12/2012 | Rosenberg et al. | |
| 8,473,216 B2 | 6/2013 | Sun | |
| 8,569,706 B2 * | 10/2013 | Thiruvenkadam | A61B 6/037 250/363.03 |
| 9,271,664 B2 * | 3/2016 | Wedan | G01R 33/287 |
| 2003/0093004 A1 * | 5/2003 | Sosa | A61B 5/04 600/544 |
| 2004/0097806 A1 | 5/2004 | Hunter et al. | |
| 2004/0254437 A1 | 12/2004 | Hauck et al. | |
| 2005/0057246 A1 | 3/2005 | Orozco et al. | |
| 2005/0137478 A1 | 6/2005 | Younge et al. | |
| 2005/0222554 A1 | 10/2005 | Wallace et al. | |
| 2005/0288577 A1 | 12/2005 | Weese | |
| 2006/0084867 A1 | 4/2006 | Tremblay et al. | |
| 2006/0095022 A1 | 5/2006 | Moll et al. | |
| 2006/0100610 A1 | 5/2006 | Wallace et al. | |
| 2007/0016007 A1 * | 1/2007 | Govari | A61B 5/063 600/424 |
| 2007/0055331 A1 * | 3/2007 | Merfeld | A61F 11/00 607/116 |
| 2007/0060833 A1 | 3/2007 | Hauck | |
| 2007/0110665 A1 | 5/2007 | Bolan et al. | |
| 2007/0181139 A1 | 8/2007 | Hauck | |
| 2008/0161681 A1 | 7/2008 | Hauck | |
| 2008/0221425 A1 | 9/2008 | Olson et al. | |
| 2008/0221643 A1 | 9/2008 | Olson | |
| 2009/0028416 A1 | 1/2009 | Floeder | |
| 2009/0067755 A1 | 3/2009 | Khamene et al. | |
| 2009/0161827 A1 | 6/2009 | Gertner | |
| 2009/0198126 A1 | 8/2009 | Klingenbeck-Regn | |
| 2010/0079158 A1 * | 4/2010 | Bar-Tal | A61B 5/042 324/705 |
| 2010/0099981 A1 | 4/2010 | Fishel | |
| 2010/0149183 A1 | 6/2010 | Loewke et al. | |
| 2010/0152571 A1 | 6/2010 | Hartmann et al. | |
| 2010/0268059 A1 | 10/2010 | Ryu et al. | |
| 2010/0298826 A1 * | 11/2010 | Leo | A61B 5/103 606/41 |
| 2011/0058239 A1 | 3/2011 | Lundvall et al. | |
| 2011/0062344 A1 | 3/2011 | Kornblau et al. | |
| 2011/0158486 A1 | 6/2011 | Cohen | |
| 2011/0158488 A1 | 6/2011 | Cohen et al. | |
| 2011/0160569 A1 | 6/2011 | Cohen | |
| 2011/0160593 A1 | 6/2011 | Deno et al. | |
| 2011/0166407 A1 | 7/2011 | Sumanaweera et al. | |
| 2011/0172927 A1 | 7/2011 | Sahasrabudhe | |
| 2011/0267340 A1 | 11/2011 | Kraus et al. | |
| 2012/0165658 A1 | 6/2012 | Shi et al. | |
| 2012/0172702 A1 | 7/2012 | Koyrakh et al. | |
| 2012/0172724 A1 | 7/2012 | Hill et al. | |
| 2012/0265054 A1 | 10/2012 | Olson | |

FOREIGN PATENT DOCUMENTS

| | | |
|---|---|---|
| EP | 1743575 | 1/2007 |
| EP | 2168478 | 3/2010 |
| JP | 2006072933 | 3/2006 |
| JP | 2007021218 A | 2/2007 |
| JP | 2010520780 A | 6/2010 |
| WO | 1998/040026 | 9/1998 |
| WO | 2001/006917 | 2/2001 |
| WO | 2008/083111 | 7/2008 |
| WO | WO 2008-083111 | 7/2008 |
| WO | 2008/112039 | 9/2008 |
| WO | 2008/112420 | 9/2008 |

OTHER PUBLICATIONS

International Search Report and Written Opinion issued in International (PCT) Patent Application No. PCT/US12/022678 (dated May 30, 2012).

International Search Report and Written Opinion issued in International (PCT) Patent Application No. PCT/US12/030925 (dated Jun. 20, 2012).

Bennink, H.E. et al., "Warping a Neuro-Anatomy Atlas on 3D MRI Data With Radial Basis Functions," Proceedings of International Conference on Biomedical Engineering (Biomed) 2006, Kuala Lumpur, Malaysia, Dec. 11-14, 2006 (4 pages).

Bookstein, Fred L., "Principal Warps: Thin-Plate Splines and the Decomposition of Deformations," 11 IEEE Transactions on Pattern Analysis and Machine Intelligence No. 6 pp. 567-585 (Jun. 1989).

Bors, Adrian G., et al., "Median Radial Basis Functions Neural Network," 7 IEEE Computational Intelligence Society No. 6, pp. 1-33 (1996).

Carr, J.C., "Reconstruction and Representation of 3D Objects With Radial Basis Functions" SIGGRAPH 01 Proceedings of the 28th Annual Conference on Computer Graphics and Interactive Techniques (10 pages) (2001).

Chui, Haili et al., "A New Algorithm for Non-Rigid Point Matching," IEEE Conference on Computer Vision and Pattern vol. 2, pp. 44-51 (2000).

Chui, Haili et al., "A New Point Matching Algorithm for Non-Rigid Registration," CVIU pp. 1-32 (Oct. 2002).

Donato, Gianluca et al., "Approximate Thin Plate Spline Mappings," ECCV 2002, LNCS 2532 (Eds. A. Heyden et al.), pp. 21-32 (2002).

(56) References Cited

OTHER PUBLICATIONS

Ebeling, H., "ASMOOTH: A simple and Efficient Algorithm for Adaptive Kernel Smoothing of Two-Dimensional Image Data," 368 Mon. Not. R. Astron. Soc. pp. 65-73 (May 2, 2006).
Jain, Ameet Kumar et al., "FTRAC—A Robust Fluoroscope Tracking Fiducial," 32 Med. Phys. No. 10 pp. 3185-3198 (Oct. 2005).
Ju, Tao, et al., "Mean Value Coordinates for Closed Triangular Meshes," 24 ACM Transactions on Graphics No. 3 pp. 561-566 (Jul. 2005).
Masson, Lucie et al., "Tracking 3D Objects Using Flexible Models," BMVC 2005.
Orr, Mark J.L., "Introduction to Radial Basis Function Networks" pp. 1-67 (1996).
Park, J. et al, "Universal Approximation Using Radial-Basis-Function Networks," 3 Neural Computation No. 2, pp. 246-57 (1991) (Abstract).
Reinsch, Christian, "Smoothing by Spline Functions," 10 Numerische Mathematik pp. 177-183 (1967).
Wiley, David F. et al., "Evolutionary Morphing," Proceedings of IEEE Visualization pp. 431-438 (2005).
Wittkampf, Fred H.M. et al. "LocalLisa: New Technique for Real-Time 3-Dimensional Localization of Regular Intracardiac Electrodes," 99 Circulation Journal of the American Heart Association pp. 1312-1317 (Mar. 16, 1999).
Rajesh, Kabra et al, Recent trends in imaging for atrial fibrillation ablation, Indian pacing and electrophysiology journal, May 5, 2010, pp. 215-227.
Bennink. H,E.; "Warping a Neuro-Anatomy Atlas an 3D MRI Data with Radial Basis Functions"; In: Proc. Intern. Conf. on Biomedical Engineering (Biomed) 2006, Kuala Lumpur, Malaysia, Reference pp. 1-4; Publication Date: Dec. 11-14, 2006.
Carr, J.C.; :"Reconstruction and Representation of 3D Objects with Radial Basis Functions"; Annual Conference of Computer Graphics SIGGRAPH; Reference pp. 67-76; Publication Date: 2001.
Author: Chui, Haili Title: A new point matching algorithm for non-rigid registration Citation: eVIU Publication Date: 2003.
Donato, Gianluca; "Approximate thin plate spline mappings"; EeeV; Reference pp. 21-31; Publication Date: 2002.
Author: Masson, Luci Title: Tracking 3D objects using flexible models Citation: BMVC Publication Date: 2005.
Wittkampf, Fred H.; "New Technique for Real-Time 3-Dimensional localization of regular intracardiac electrodes"; Circulation—Journal of the American Heart Association; Reference pp. 1312-1317; Publication Date: Mar. 1999.
Bookstein, Fred L.; "Thin-Plate splines and the atlas problem for biomedical images"; Lecture Notes in Computer Science, vol. 511/1991 Reference Pages: Abstract Publication Date: 1991.
International Search Report and Written Opinion in PCT Application No. PCT/US2013/045885 (dated Oct. 1, 2013).
Kabra, Rajesh et al., "Recent trends in imaging for atrial fibrillation ablation", Indian Pacing and Electrophysiology Journal, pp. 215-227, May 5, 2010.
Reinsch, Christian; "Smoothing by Spline Functions"; Citation: 13 Numer. Math. Bd. 10 Reference pp. 177-183 Publication Date: 1967.
Title: Definition: interpolate Citation: Collins English Dictionary—Complete and Unabridged 10th Edition, 2009, Harper Collins Publishers Publication Date: 2009.
International Search Report & Written Opinon in PCT Application No. PCT/US2012/030925 (dated Jun. 20, 2012).
Supplementary European Search Report in EP Application No. 12831765.8 (dated Mar. 10, 2015).
Supplementary Partial European Search Report in EP Application No. 12770539.0 (dated Dec. 4, 2014).
George Roussos, Brad J.C. Baxter, "Rapid evaluation of radial basis functions", 2005, Journal of Computational and Applied Mathematics, vol. 180, pp. 51-70.
"3D Photography: Point Based Rigid Registration" http://www1.cs.columbia.edu/~allen/PHOTOPAPERS/hmwk.1.pdf, downloaded Aug. 15, 2017.

\* cited by examiner

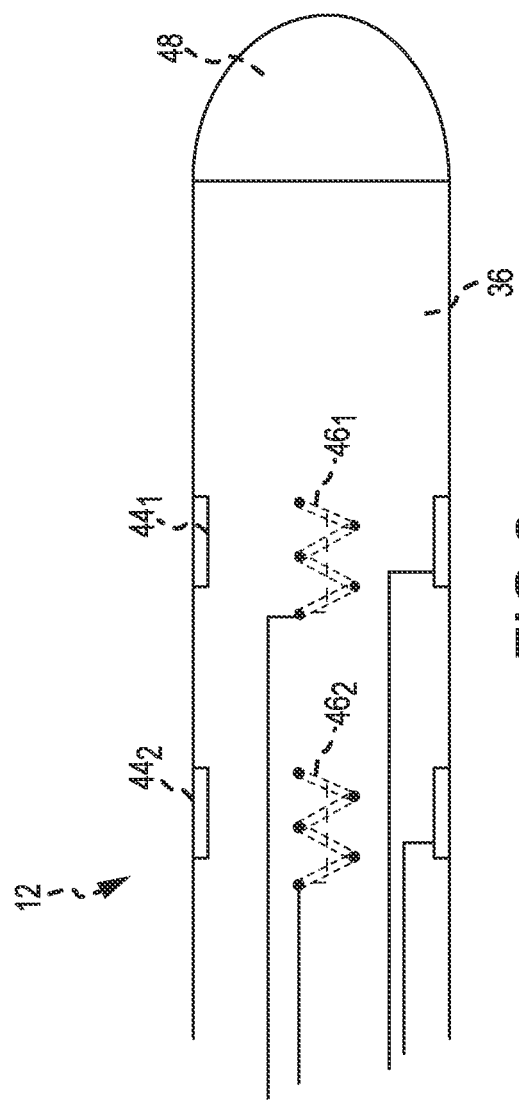

CORRECTION OF SHIFT AND DRIFT IN IMPEDANCE-BASED MEDICAL DEVICE NAVIGATION USING MAGNETIC FIELD INFORMATION

CROSS-REFERENCE TO RELATED APPLICATIONS

The present application is a continuation-in-part of and claims the benefit of priority to U.S. patent application Ser. No. 13/087,203, filed on Apr. 14, 2011, now U.S. Pat. No. 9,901,303. The present application is also a continuation-in-part of and claims the benefit of priority to U.S. patent application Ser. No. 13/231,284, filed Sep. 13, 2011, now pending, both of which are hereby incorporated by reference in their entirety as though fully set forth herein.

BACKGROUND OF THE INVENTION a. Field of the Invention

This invention relates to a system and method for navigating a medical device within a body. In particular, the instant invention relates to a system and method that enable correction of drift and shift in impedance levels in electric field based position and navigation systems.

b. Background Art

A wide variety of medical devices are inserted into the body to diagnose and treat various medical conditions. Catheters, for example, are used to perform a variety of tasks within human bodies and other bodies including the delivery of medicine and fluids, the removal of bodily fluids and the transport of surgical tools and instruments. In the diagnosis and treatment of atrial fibrillation, for example, catheters may be used to deliver electrodes to the heart for electrophysiological mapping of the surface of the heart and to deliver ablative energy to the surface among other tasks. Catheters are typically routed to a region of interest through the body's vascular system. In a conventional approach, an introducer is used to puncture the skin surface and a sheath having an inner diameter greater than the outer diameter of the catheter is threaded through the vasculature to a region of interest. The catheter is then moved longitudinally through the sheath to the region of interest either manually by a clinician or through the use of electromechanical drive systems.

It is desirable to track the position of medical devices such as catheters as they are moved within the body so that, for example, drugs and other forms of treatment are administered at the proper location and medical procedures can be completed more efficiently and safely. One conventional means to track the position of medical devices within the body is fluoroscopic imaging. Fluoroscopy is disadvantageous, however, because it subjects the patient and physician to undesirable levels of electromagnetic radiation. As a result, medical device navigation systems have been developed to track the position of medical devices within the body. These systems typically rely on the generation of electrical or magnetic fields and the detection of induced voltages and currents on position sensors attached to the medical device and/or external to the body. The information derived from these systems is then provided to a physician through, for example, a visual display.

One conventional medical device navigation system is made available under the trademark "ENSITE NAVX" by St. Jude Medical, Inc. The system is based on the principle that when electrical currents are passed through the thorax a voltage drop occurs across internal organs such as the heart and this voltage drop can be measured and used to determine the position of a medical device within the body. The system includes three pairs of patch electrodes that are placed on opposed surfaces of the body (e.g., chest and back, left and right sides of the thorax, and neck and leg) and form generally orthogonal x, y, and z axes as well as a reference electrode that is typically placed near the stomach and provides a reference value and acts as the origin of the coordinate system for the navigation system. Sinusoidal currents are driven through each pair of patch electrodes and voltage measurements for one or more electrodes associated with the medical device are obtained. The measured voltages are proportional to the distance of the device electrodes from the patch electrodes. The measured voltages are compared to the potential at the reference electrode and a position of the device electrodes within the coordinate system of the navigation system is determined.

The above-described system can be used to provide a substantially accurate indication of the position of the medical device within a body. Electric field based navigation systems, however, are subject to various types of interference that can impact the accuracy of position measurements. For example, the level of electrical impedance in the patient body is not necessarily constant. The impedance can slowly drift or even undergo transient shifts due to, for example, a change in medication leading to drift and/or shift in the detected position of the medical device. Various methods have been proposed to mitigate potential drift or shift including bio-impedance scaling, patch center subtraction and the use of a fixed reference catheter with a reference electrode. Bio-impedance scaling and patch center subtraction help to reduce drift and shift, but do not eliminate all cases of drift and shift. The use of a fixed reference catheter requires insertion of an additional catheter into the body thereby increasing procedure time and the risk of complications. Further, the reference catheter may become dislodged during the procedure.

There is thus an ongoing a need for a system and method for navigating a medical device within a body that will minimize and/or eliminate one or more of the above-identified deficiencies.

BRIEF SUMMARY OF THE INVENTION

The present disclosure relates to a system and method for navigating a medical device within a body. In particular, the present disclosure relates to a system and method that reduce or eliminate potential errors in position detection due to drift or shifts in patient impedance.

A system for navigating a medical device within a body includes an electronic control unit configured to determine an operating position for an electrical position sensor on the medical device within a first coordinate system. The first coordinate system is defined by an electric field based positioning system. The electronic control unit is further configured to determine an operating position for a magnetic position sensor on the medical device within a second coordinate system. The second coordinate system is defined by a magnetic field based positioning system. The magnetic position sensor is disposed proximate the electrical position sensor. The electronic control unit is further configured to apply a mapping function correlating the operating positions of the electrical position sensor and the magnetic position sensor. The mapping function generates a mapped position for the magnetic position sensor in the first coordinate system responsive to the operating position of the magnetic position sensor in the second coordinate system. The electronic control unit is further configured to determine an adjusted operating position for the electrical position sensor in the first coordinate system responsive to the mapped position of the magnetic position sensor.

A method for navigating a medical device within a body includes determining an operating position for an electrical position sensor on the medical device within a first coordinate system. The first coordinate system is defined by an electric field based positioning system. The method further includes determining an operating position for a magnetic position sensor on the medical device within a second coordinate system. The second coordinate system is defined by a magnetic field based positioning system. The magnetic position sensor is disposed proximate the electrical position sensor. The method further includes applying a mapping function correlating the operating positions of the electrical position sensor and the magnetic position sensor. The mapping function generates a mapped position for the magnetic position sensor in the first coordinate system responsive to the operating position of the magnetic position sensor in the second coordinate system. The method further includes determining an adjusted operating position for the electrical position sensor in the first coordinate system responsive to the mapped position of the magnetic position sensor.

The system and method enable consistent correction of errors in position measurements due to shift or drift in patient impedance levels. Further, the system and method do not require the use of an additional reference catheter and the resulting increases in procedure time and risks.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 2 is a cross-sectional view of a portion of an exemplary medical device for use in the system of FIG. 1.

DETAILED DESCRIPTION OF THE INVENTION

Figure 1:
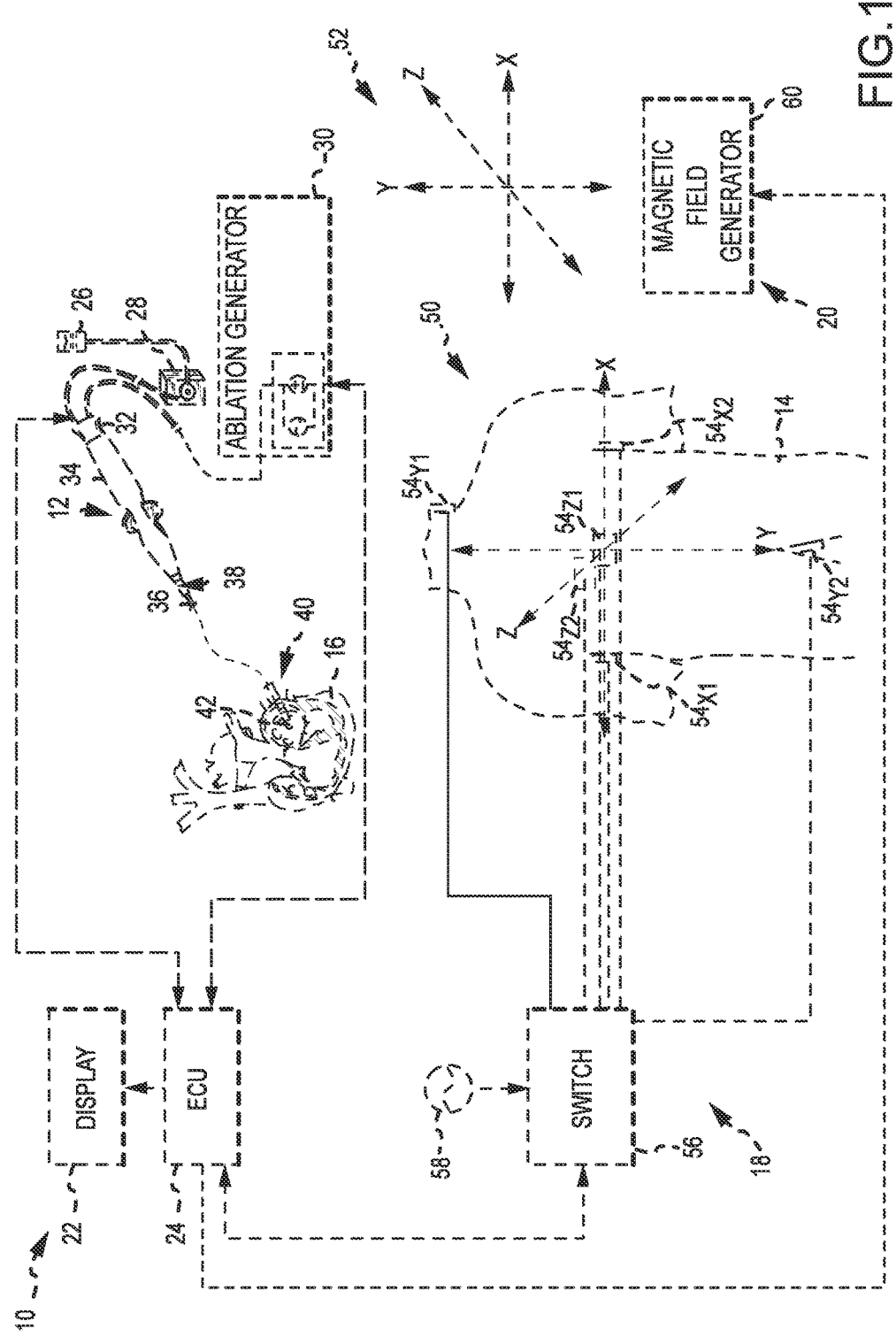
FIG. 1 is diagrammatic view of one embodiment of a system for navigating a medical device within a body in accordance with the present teachings.

Referring now to the drawings wherein like reference numerals are used to identify identical components in the various views, FIG. 1 illustrates one embodiment of a system 10 for navigating a medical device within a body 12. In the illustrated embodiment, the medical device comprises a catheter 14 and, in particular, an irrigated ablation catheter for use in diagnosis or treatment of cardiac tissue 16 in body 12. It should be understood, however, that a system 10 in accordance with the present teachings may find application in connection with a wide variety of medical devices used within body 12 for diagnosis or treatment. For example, system 10 may be used to navigate an electrophysiological (EP) mapping catheter or an intradcardiac echocardiography (ICE) catheter. Further, it should be understood that the system may be used to navigate medical devices used in the diagnosis or treatment of portions of body 12 other than the tissue 16. System 10 may include an electric field based positioning system 18, a magnetic field based positioning system 20, a display 22 and an electronic control unit (ECU) 24.

Catheter 14 is provided for examination, diagnosis and treatment of internal body tissues such as cardiac tissue 16. In accordance with one embodiment, catheter 14 comprises an ablation catheter and, more particularly, an irrigated radio-frequency (RF) ablation catheter. It should again be understood, however, that catheter 14 is provided for illustration only and that system 10 could be adapted for use with a variety of catheters including, for example, electrophysiology mapping catheters and intracardiac echocardiograph (ICE) catheters, as well as for use with other types of ablation catheters including those providing different types of ablation energy (e.g., cryoablation, ultrasound, etc.). Catheter 14 is connected to a fluid source 26 having a biocompatible fluid such as saline through a pump 28 (which may comprise, for example, a fixed rate roller pump or variable volume syringe pump with a gravity feed supply from fluid source 26 as shown) for irrigation. Catheter 14 is also electrically connected to an ablation generator 30 for delivery of RF energy. Catheter 14 may include a cable connector or interface 32, a handle 34, a shaft 36 having a proximal end 38 and a distal end 40 (as used herein, "proximal" refers to a direction toward the end of the catheter near the physician, and "distal" refers to a direction away from the physician and (generally) inside the body of a patient) and one or more electrodes 42. Referring to FIG. 2, in accordance with one aspect of the present teachings, catheter 14 further includes one or more electrical position sensors $44_1$, $44_2$ and one or more magnetic position sensors $46_1$, $46_2$ for a purposed described hereinbelow. Catheter 14 may also include other conventional components not illustrated herein such as a temperature sensor, additional electrodes, and corresponding conductors or leads.

Connector 32 provides mechanical, fluid and electrical connection(s) for conduits or cables extending from pump 28, and ablation generator 30. Connector 32 is conventional in the art and is disposed at a proximal end 38 of catheter 14.

Handle 34 provides a location for the physician to hold catheter 14 and may further provides means for steering or guiding shaft 36 within body 12. For example, handle 34 may include means to change the length of a guidewire extending through catheter 14 to distal end 40 of shaft 46 to steer distal end 40 and, thus, shaft 36. Handle 34 is also conventional in the art and it will be understood that the construction of handle 34 may vary.

Shaft 36 is an elongated, flexible member configured for movement within body 12. Shaft 36 supports electrodes 42, position sensors $44_1$, $44_2$, $46_1$, $46_2$, associated conductors, and possibly additional electronics used for signal processing or conditioning. Shaft 36 may also permit transport, delivery, and/or removal of fluids (including irrigation fluids and bodily fluids), medicines, and/or surgical tools or instruments. Shaft 36 may be made from conventional materials such as polyurethane and defines one or more lumens configured to house and/or transport electrical conductors, fluids, or surgical tools. Shaft 36 may be introduced into a blood vessel or other structure within body 12 through a conventional introducer sheath. Shaft 36 may then be steered or guided through body 12 to a desired location such as tissue 16 using guide wires or pullwires or other means known in the art including remote control guidance systems.

Electrodes 42 may be provided for a variety of diagnostic and therapeutic purposes including, for example, electrophysiological studies, catheter identification and location, pacing, and cardiac mapping and ablation. Referring to FIG. 2, in the illustrated embodiment, catheter 14 includes an ablation tip electrode 48 at distal end 40 of shaft 36. It should be understood, however, that the number, orientation, and purpose of electrodes 42 may vary.

Electrical position sensors $44_1$, $44_2$ are provided for use in determining the position of catheter 14 within body 12. Sensors $44_1$, $44_2$ are conventional in the art. In the illustrated embodiment, sensors $44_1$, $44_2$ comprise electrodes and, in particular, conventional ring electrodes located proximal to the distal end 40 of catheter shaft 36 and tip electrode 48. As sensors $44_1$, $44_2$ move within body 14, and within the electric field generated by system 18, the voltage readings from sensors $44_1$, $44_2$ change thereby indicating the location of sensors $44_1$, $44_2$ within the electric field and with a coordinate system 50 established by system 18. Sensors $44_1$, $44_2$ communicate position signals to ECU 24 through a conventional interface (not shown).

Magnetic position sensors $46_1$, $46_2$ are also provided for use in determining the position of catheter 14 within body 12. Sensors $46_1$, $46_2$ are conventional in the art. In the illustrated embodiment, sensors $46_1$, $46_2$ are coils. As sensors $46_1$, $46_2$ move within body 14, and within the magnetic field generated by system 20, the current output of each sensor $46_1$, $46_2$ changes thereby indicating the location of sensors $46_1$, $46_2$ within the magnetic field and with a coordinate system 52 established by system 20. Sensors $46_1$, $46_2$ may be wound about catheter 14 at or near distal end 40 and may be embedded within the walls of catheter 14 such that sensors $46_1$, $46_2$ are insulated. Alternatively, sensors $46_1$, $46_2$ could be embedded further within catheter 14 as shown in FIG. 2, or could be placed at other locations within the catheter 14. Sensors $46_1$, $46_2$ may also have appropriate insulation and/or shielding (e.g., a conductive foil or wire mesh) to cancel potential interferences from other devices near body 12. It should be understood that sensors $46_1$, $46_2$ may take forms other than the form illustrated in FIG. 2. Sensors $46_1$, $46_2$ may, for example, comprise any conventional position sensors for detecting changes in magnetic fields including Hall effect sensors, magnetoresistive sensors and sensors made from magnetoresistive materials and piezoelectric materials and the like. Sensors $46_1$, $46_2$ communicate position signals to ECU 24 through a conventional interface (not shown). In accordance with one aspect of the present teachings, each of magnetic position sensors $46_1$, $46_2$ is disposed proximate to a corresponding electrical position sensor $44_1$, $44_2$ such that the detected position of one of sensors 44, 46 may be indicative of the position of the other corresponding sensor 44, 46. The magnetic position sensors $46_1$, $46_2$ may, for example be located from about 1.0 to about 3.0 millimeters from a corresponding electrical position sensor $44_1$, $44_2$ and may be centered between two electrical position sensors $44_1$, $44_2$ which may be spaced about 2.0 to 6.0 millimeters apart.

System 18 is provided to determine the position and orientation of catheter 14 and similar devices within body 12. System 18 may comprise the system made available under the trademark "ENSITE NAVX" by St. Jude Medical, Inc. and described, for example, in U.S. Pat. No. 7,263,397 titled "Method and Apparatus for Catheter Navigation and Location Mapping in the Heart," the entire disclosure of which is incorporated herein by reference. The system is based on the principle that when low amplitude electrical signals are passed through the thorax, body 12 acts as a voltage divider (or potentiometer or rheostat) such that the electrical potential or field strength measured at an electrode such as one of position sensors $44_1$, $44_2$ on catheter 14 may be used to determine the position of the electrode, and therefore catheter 14, relative to a pair of external patch electrodes using Ohm's law and the relative location of a reference electrode (e.g. in the coronary sinus). In one configuration, the system includes three pairs of patch electrodes 54 that are placed on opposed surfaces of body 12 (e.g., chest and back, left and right sides of the thorax, and neck and leg) and form generally orthogonal x, y, and z axes as well as a reference electrode/patch (not shown) that is typically placed near the stomach and provides a reference value and acts as the origin of the coordinate system 50 for the navigation system. Sinusoidal currents are driven through each pair of patch electrodes 54 and voltage measurements for one or more position sensors $44_1$, $44_2$ associated with catheter 14 are obtained. The measured voltages are a function of the distance of the position sensors $44_1$, $44_2$ from the patch electrodes 54. The measured voltages are compared to the potential at the reference electrode and a position of the position sensors $44_1$, $44_2$ within the coordinate system 50 of the navigation system is determined. In accordance with this exemplary system, system 18 may include patch electrodes 54 (namely $54_{X1}$, $54_{X2}$, $54_{Y1}$, $54_{Y2}$, $54_{Z1}$, $54_{Z2}$) a switch 56, and a signal generator 58.

Patch electrodes 54 are provided to generate electrical signals used in determining the position of catheter 14 within three-dimensional coordinate system 50 of system 18. Electrodes 54 may also be used to generate EP data regarding tissue 16. Electrodes 54 are placed orthogonally on the surface of body 12 and are used to create axes specific electric fields within body 12. Electrodes $54_{X1}$, $54_{X2}$ may be placed along a first (x) axis. Similarly, electrodes $54_{Y1}$, $54_{Y2}$ may be placed along a second (y) axis, and electrodes $54_{Z1}$, $54_{Z2}$ may be placed along a third (z) axis. Each of the electrodes 54 may be coupled to multiplex switch 56. ECU 24 is configured through appropriate software to provide control signals to switch 56 and thereby sequentially couple pairs of electrodes 54 to signal generator 58. Excitation of each pair of electrodes 54 generates an electromagnetic field within body 14 and within an area of interest such as the heart. Voltage levels at non-excited electrodes 54 may be filtered and converted and provided to ECU 24 for use as reference values.

System 20 is also provided to determine the position and orientation of catheter 14 and similar devices within body 12. System 20 comprises a system that employs magnetic fields to detect the position of catheter 14 within body 12 such as the system made available under the trademark "GMPS" by MediGuide, Ltd. and generally shown and described in, for example, U.S. Pat. No. 7,386,339 titled "Medical Imaging and Navigation System," the entire disclosure of which is incorporated herein by reference. In such a system, a magnetic field generator 60 may be employed having three orthogonally arranged coils, arranged to create a magnetic field within body 12 and to control the strength, orientation, and frequency of the field. The magnetic field generator 60 may be located above or below the patient (e.g., under a patient table) or in another appropriate location. Magnetic fields are generated by the coils and current or voltage measurements for one or more position sensors $46_1$, $46_2$ associated with catheter 14 are obtained. The measured currents or voltages are proportional to the distance of the sensors $46_1$, $46_2$ from the coils thereby allowing a position of the sensors $46_1$, $46_2$ within a coordinate system 52 of system 20.

Display 22 is provided to convey information to a physician to assist in diagnosis and treatment. Display 22 may comprise one or more conventional computer monitors or other display devices. Display 22 may present a graphical user interface (GUI) to the physician. The GUI may include a variety of information including, for example, an image of the geometry of tissue 16, electrophysiology data associated with the tissue 16, graphs illustrating voltage levels over time for various electrodes 42, and images of catheter 14 and other medical devices and related information indicative of the position of catheter 14 and other devices relative to the tissue 16.

ECU 24 provides a means for controlling the operation of various components of system 10 including catheter 14 and ablation generator 30, switch 56 of system 18, and magnetic generator 60 of system 20. ECU 24 may also provides a means for determining the geometry of tissue 16, electrophysiology characteristics of tissue 16 and the position and orientation of catheter 12 relative to tissue 16 and body 14. ECU 24 also provides a means for generating display signals used to control display 22. ECU 24 may comprise one or more programmable microprocessors or microcontrollers or may comprise one or more application specific integrated circuits (ASICs). ECU 24 may include a central processing unit (CPU) and an input/output (I/O) interface through which ECU 24 may receive a plurality of input signals including signals generated by ablation generator 30, electrodes 42 and position sensors $44_1$, $44_2$, $46_1$, $46_2$ on catheter 14, and patch electrodes 54 of system 18, and generate a plurality of output signals including those used to control and/or provide data to catheter 14, display 22, ablation generator 30, switch 56 of system 18, and generator 60 of system 20.

Figure 3A:
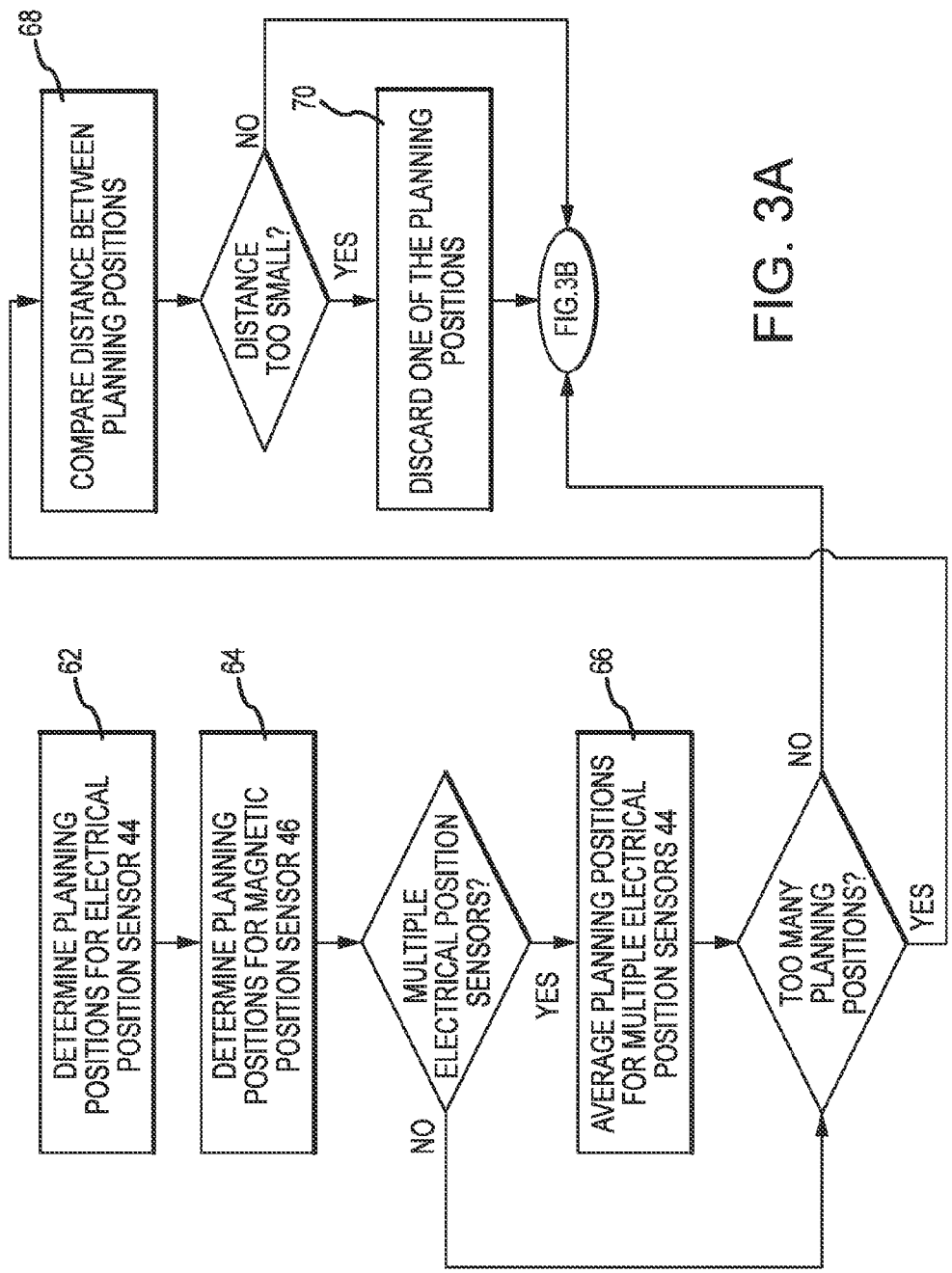
FIG. 3A-C is a flow-chart diagram illustrating one embodiment of a method for navigating a medical device within a body in accordance with the present teachings.
Figure 3B:
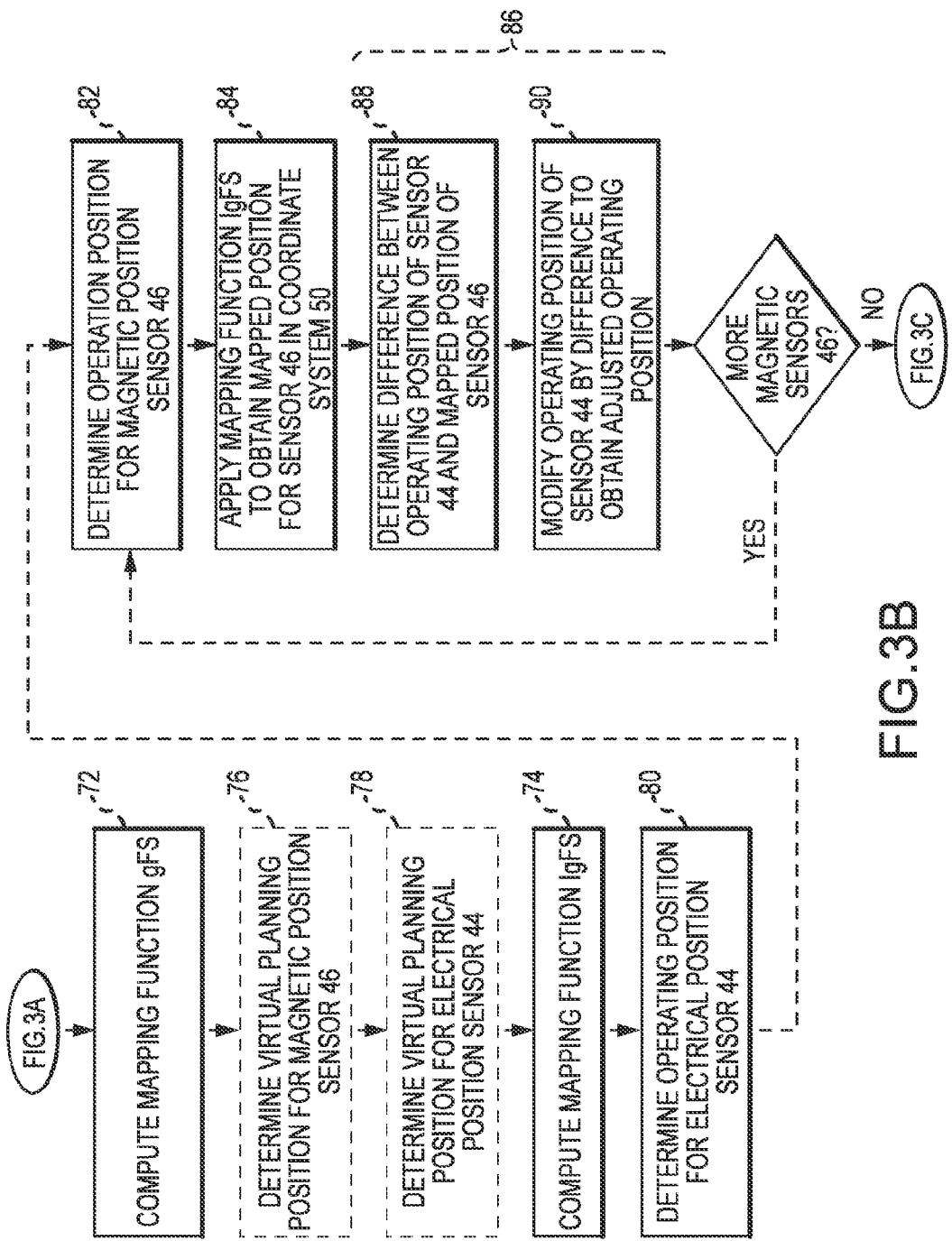
Figure 3C:
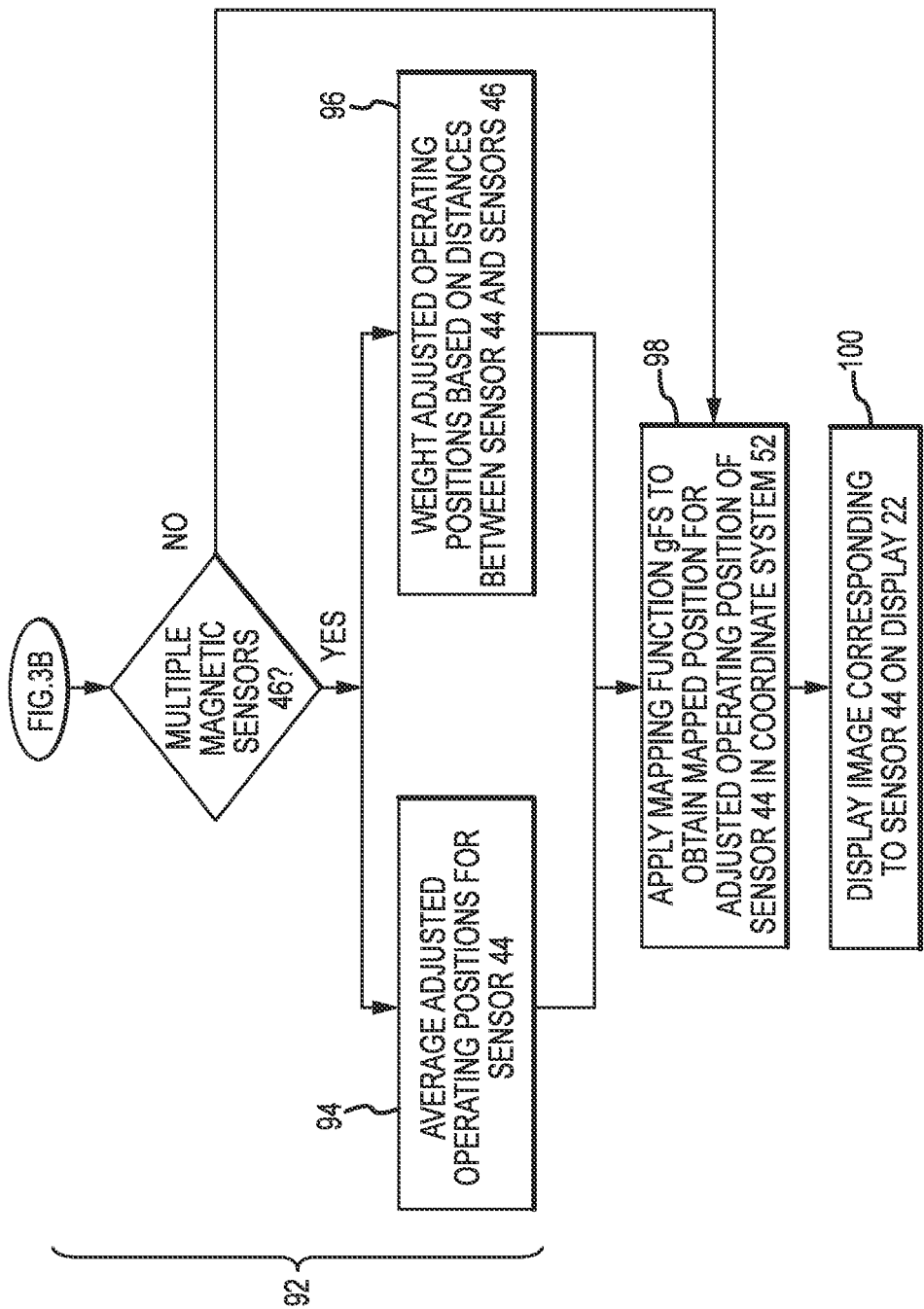

In accordance with the present teachings, ECU 24 may be configured with programming instructions from a computer program (i.e., software) to implement a method for navigating catheter 14 within body 12. The program may be stored in a computer storage medium such as a memory (not shown) that is internal to ECU 24 or external to ECU 24 and may be pre-installed in the memory or obtained from a computer storage medium external to device 10 including from various types of portable media (e.g., compact discs, flash drives, etc.) or file servers or other computing devices accessible through a telecommunications network. Referring to FIG. 3, the method may begin with the steps 62, 64 of determining planning positions for an electrical position sensor $44_1$ and a magnetic position sensor $46_1$ within coordinate systems 50, 52, respectively. During a planning stage for a diagnostic or treatment procedure, catheter 14 (or another type of medical device having sensors $44_1$, $46_1$) is disposed within the region of interest (e.g., a chamber of the heart) within coordinate systems 50, 52. Sampling of the sensors $44_1$, $46_1$ is performed to collect pairs of correlated planning positions (also referred to as reference points or fiducials). Each planning position is a pair of three-dimensional electrically or magnetically measured coordinates of the form:

$$\{nX_j, nY_j, nZ_j\}$$

and $$\{gX_j, gY_j, gZ_j\}$$

where n refers to a point in coordinate system 50 of the electric field based position system 18, g refers to a point in coordinate system 52 of the magnetic field based position system 20, and j=1, 2, . . . N with N being the total number of planning positions. It should be understood that steps 62, 64 may be performed substantially simultaneously. It should also be understood that the steps may be performed for multiple electrical and magnetic position sensors 44, 46 on catheter 14. In some devices, multiple electrical position sensors 44 may be disposed proximate to a single magnetic position sensor 46 thereby resulting in the generation of a plurality of electrical planning positions for each magnetic planning position. In such cases, the method may further include the step 66 of averaging the planning positions for the electrical position sensors 44 disposed proximate the magnetic position sensor 46. The determination of planning positions for sensors 44, 46 on catheter 14 may generate more positions than required or desired. Therefore, the method may further include the step 68 of comparing a distance between a pair of planning positions for either a single sensor (e.g., electrical position sensor $44_1$ or magnetic position sensor $46_1$) or multiple sensors (e.g., electrical position sensors $44_1$ and $44_2$) and the step 70 of discarding one of the planning positions if the distance meets a predetermined characteristic relative to a predetermined threshold (e.g., is less than a predetermined distance such as 4.0 millimeters).

Once the planning positions are obtained, the planning stage may continue with the steps 72, 74 of computing mapping functions responsive to the planning positions for the electrical and magnetic position sensors $44_1$, $46_1$. One mapping function correlates the planning positions for the electrical position sensor $44_1$ and the magnetic position sensor $46_1$ such that the mapping function generates a mapped position for the electrical position sensor $44_1$ in the coordinate system 52 of the magnetic-field based positioning system 20 responsive to a position of the electrical position sensor in the coordinate system 50 of the electric-field based positioning system 18. The mapping function may be computed using radial basis function or thin plate spline interpolation with the basis function chosen as r and a non-zero stiffness parameter $\lambda$ so that the registration between the coordinate systems 50, 52 is not rigid and the mapping is smooth without over-fitting noisy measurements. The basis function used for interpolation is selected from a range of the radial basis functions. One possible choice for the set of functions is:

$$\psi_i(\vec{nX}) = |\vec{nX} - \vec{nX_i}|$$

Where $\vec{nX}$ is the vector notation for the planning position $\{nX_j, nY_j, nZ_j\}$ (similarly, as referenced hereinbelow, $\vec{gX}$ will represent the vector notation for the planning position $\{gX_j, gY_j, gZ_j\}$) and each function has a center at the corresponding point $\vec{nX_i}$. The right hand side of the above equation may be expressed in standard notation as:

$$|\vec{x} - \vec{x}_i| = \sqrt{(x-x_i)^2 + (y-y_i)^2 + (z-z_i)^2}$$

A map from coordinate system 50 to coordinate system 52 may be represented by the following functions:

$$gX(nX, nY, nZ) = b_1^x nX + b_2^x nY + b_3^x nZ + c^x + \sum_{j=1}^{N} a_j^x \psi_j(\vec{nX})$$

$$gY(nX, nY, nZ) = b_1^y nX + b_2^y nY + b_3^y nZ + c^y + \sum_{j=1}^{N} a_j^y \psi_j(\vec{nX})$$

-continued $$gZ(nX, nY, nZ) = b_1^z nX + b_2^z nY + b_3^z nZ + c^z + \sum_{j=1}^{N} a_j^z \psi_j(\vec{nX})$$

Where $a_j^x, a_j^y, a_j^z, b_j^x, b_j^y, b_j^z$ and $c^x, c^y, c^z, j=1, 2 \ldots N$, and $i=1, 2, 3$ are parameters chosen such that the planned positions are mapped as close as possible to measured positions and the degree of closeness is controlled by the smoothing parameter $\lambda$. The following equations then define the unknown parameters by providing a system of linear equations for a similar number of unknown parameters:

$$gX_i = b_1^x nX_i + b_2^x nY_i + b_3^x nZ_i + c^x + \sum_{j=1}^{N} a_j^x \left( \psi_j(\vec{nX_i}) - \lambda \delta_{ij} \right)$$

$$gY_i = b_1^y nX_i + b_2^y nY_i + b_3^y nZ_i + c^y + \sum_{j=1}^{N} a_j^y \left( \psi_j(\vec{nX_i}) - \lambda \delta_{ij} \right)$$

$$gZ_i = b_1^z nX_i + b_2^z nY_i + b_3^z nZ_i + c^z + \sum_{j=1}^{N} a_j^z \left( \psi_j(\vec{nX_i}) - \lambda \delta_{ij} \right)$$

$$\sum_{j=1}^{N} a_j^k = 0, \sum_{j=1}^{N} a_j^k nX_j = 0, \sum_{j=1}^{N} a_j^k nY_j = 0,$$

$$\sum_{j=1}^{N} a_j^k nZ_j = 0, k = x, y, z,$$

Where $\delta_{ij}$ are the Kronecker symbols defined by the following equations:

$\delta_{ij}=1, i=j$ $\delta_{ij}=0, i \neq j$

The solution to these equations can be used to define the mapping function gFS which can be applied as follows to map a position in coordinate system 50 into coordinate system 52:

$$\vec{gX} = gFS(\vec{nX})$$

Further information regarding the above steps may be found in U.S. patent application Ser. No. 13/231,284 filed Sep. 13, 2011, the entire disclosure of which is incorporated herein by reference.

The mapping function gFS may be used to detect shift or drift in the readings obtained by electric-field based positioning system 18 by applying the function to a position measurement for an electric position sensor 44₁ as follows:

$$\vec{gX_{44_1}} = gFS(\vec{nX_{44_1}})$$

The result can be compared against the position measurement for a corresponding magnetic sensor 46₁ in coordinate system 52 to obtain the required correction:

$$\vec{g\Delta} = \vec{gX_{46_1}} - \vec{gX_{44_1}}$$

This correction can then be applied to correct the locations of each electrical position sensor 44 within coordinate system 52:

$$\vec{gX_{corr}^k} = \vec{g\Delta} + \vec{gX^k}$$

Because the mapping function gFS is highly non-linear, global homogenous shifts in coordinate system 50 may not be properly corrected by applying the function. In accordance with one aspect of the present teachings, therefore, the use of an inverse mapping function IgFS has been developed to compensate for drifts and shift directly within coordinate system 50 before mapping function gFS is applied. Accordingly, in step 74 a mapping function is computed that correlates the planning positions for the electrical position sensor 44₁ and the magnetic position sensor 46₁ such that the mapping function generates a mapped position for the magnetic position sensor 46₁ in the coordinate system 50 of the electric-field based positioning system 18 responsive to a position of the magnetic position sensor 46₁ in the coordinate system 52 of the magnetic-field based positioning system 20. The mapping function IgFS can be computed using equations similar to those used to compute the mapping function gFS by using the same basis functions and interchanging the magnetic and electrical planning positions. Thus, a map from coordinate system 52 to coordinate system 50 may be represented by the following functions:

$$nX(gX, gY, gZ) = \tilde{b}_1^x gX + \tilde{b}_2^x gY + \tilde{b}_3^x gZ + \tilde{c}^x + \sum_{j=1}^{N} \tilde{a}_j^x \psi_j(\vec{gX})$$

$$nY(gX, gY, gZ) = \tilde{b}_1^y gX + \tilde{b}_2^y gY + \tilde{b}_3^y gZ + \tilde{c}^y + \sum_{j=1}^{N} \tilde{a}_j^y \psi_j(\vec{gX})$$

$$nZ(gX, gY, gZ) = \tilde{b}_1^z gX + \tilde{b}_2^z gY + \tilde{b}_3^z gZ + \tilde{c}^z + \sum_{j=1}^{N} \tilde{a}_j^z \psi_j(\vec{gX})$$

Where $\tilde{a}_j^x, \tilde{a}_j^y, \tilde{a}_j^z, \tilde{b}_j^x, \tilde{b}_j^y, \tilde{b}_j^z$ and $\tilde{c}^x, \tilde{c}^y, \tilde{c}^z, j=1, 2 \ldots N$, and $i=1, 2, 3$ are parameters chosen such that the planned positions are mapped as close as possible to measured positions and the degree of closeness is controlled by the smoothing parameter $\lambda$. The following equations then define the unknown parameters by providing a system of linear equations for a similar number of unknown parameters:

$$nX_i = \tilde{b}_1^x gX_i + \tilde{b}_2^x gY_i + \tilde{b}_3^x gZ_i + \tilde{c}^x + \sum_{j=1}^{N} \tilde{a}_j^x \left( \psi_j(\vec{gX_i}) - \lambda \delta_{ij} \right)$$

$$nY_i = \tilde{b}_1^y gX_i + \tilde{b}_2^y gY_i + \tilde{b}_3^y gZ_i + \tilde{c}^y + \sum_{j=1}^{N} \tilde{a}_j^y \left( \psi_j(\vec{gX_i}) - \lambda \delta_{ij} \right)$$

$$nZ_i = \tilde{b}_1^z gX_i + \tilde{b}_2^z gY_i + \tilde{b}_3^z gZ_i + \tilde{c}^z + \sum_{j=1}^{N} \tilde{a}_j^z \left( \psi_j(\vec{gX_i}) - \lambda \delta_{ij} \right)$$

$$\sum_{j=1}^{N} \tilde{a}_j^k = 0, \sum_{j=1}^{N} \tilde{a}_j^k gX_j = 0, \sum_{j=1}^{N} \tilde{a}_j^k gY_j = 0,$$

$$\sum_{j=1}^{N} \tilde{a}_j^k gZ_j = 0, k = x, y, z,$$

Where $\delta_{ij}$ are the Kronecker symbols defined by the following equations:

$\delta_{ij}=1, i=j$ $\delta_{ij}=0, i \neq j$

The solution to these equations can be used to define the mapping function IgFS which can be applied as follows to map a position in coordinate system 52 into coordinate system 50:

$$\vec{nX} = IgFS(\vec{gX})$$

Although FIG. 3 illustrates steps 72, 74 as occurring in succession, it should be understood that the order of steps 72, 74 could be reversed and or, in other embodiments the steps 72, 74 may be performed simultaneously.

Although the mapping function IgFS is intended to be the inverse of the mapping function gFS, the function is only an approximate inverse. Thus, sequential application of the mapping functions yields a position that is only an approximate of the original position:

$$\vec{nX} \approx IgFS(gFS(\vec{nX}))$$

In order to make the mapping function IgFS closer to a true inverse of the mapping function gFS, the method may utilize additional planning positions and, in particular, virtual planning positions. Accordingly, the method may optionally include the steps 76, 78 of determining a virtual planning position for electrical position sensor $44_1$ within coordinate system 50 and a corresponding virtual planning position for magnetic position sensor $46_1$ within coordinate system 52. The virtual planning position for position sensor $44_1$ may be located at a boundary in coordinate system 50. The corresponding virtual planning position for position sensor $46_1$ could then be obtained by applying the mapping function gFS to the virtual planning position for position sensor $44_1$ (in this embodiment, it should be understood that the step 74 would follow step 72 sequentially). The virtual planning positions may approximate a grid pattern on a surface surrounding the planning positions determined in steps 62, 64. The surface may comprise the faces of an axis-aligned rectangular parallelepiped enclosing those planning positions. Alternatively, the virtual planning positions may also approximate the volume in which the planning positions reside if computational resources are sufficient. The number of virtual planning positions may be restricted to a number that is less than the number of planning positions obtained in steps 62, 64 for computational efficiency.

Once the mapping functions gFS and IgFS have been computed, an operating stage of the diagnostic or treatment procedure may commence through which catheter 14 or another medical device may be maneuvered within body 12 to a region of interest. The method may therefore continue with the step 80 of determining an operating position for electrical position sensor $44_1$ within coordinate system 50 of electric field based positioning system 18 and the step 82 of determining an operating position for magnetic position sensor $46_1$, disposed proximate position sensor $44_1$, within coordinate system 52 of magnetic field based positioning system 20. The method may then proceed with the step 84 of applying mapping function IgFS to generate a mapped position for magnetic position sensor $46_1$ in coordinate system 50 responsive to the operating position of magnetic position sensor $46_1$ in coordinate system 52. Once the mapped position is obtained, the method may continue with the step 86 of determining an adjusted or corrected operating position for electrical position sensor $44_1$ in coordinate system 50 responsive to the mapped position of magnetic position sensor $46_1$. In particular, step 86 may include the substep 88 of determining a difference between the operating position for electrical position sensor $44_1$ in coordinate system 50 and the mapped position for magnetic position sensor $46_1$ in coordinate system 50:

$$\vec{\Delta}_1 = IgFS(\vec{g46_1}) - \vec{n44_1}$$

Step 86 may further include the substep 90 of modifying the operating position for electrical position sensor $44_1$ in coordinate system 50 by the difference to obtain the adjusted or corrected operating position of electrical position sensor $44_1$ in coordinate system 50:

$$\vec{n44}_{1corr} = \vec{n44}_1 + \vec{\Delta}_1$$

The adjusted operating position thereby accounts for drift and shift resulting from changes in impedance in body 12 by correlating the position of electrical position sensor $44_1$ with the position of magnetic position sensor $46_1$ in coordinate system 50. Because the position of magnetic position sensor $46_1$ in coordinate system 50 as detected by magnetic positioning system 20 is not subject to the changes in impedance, mapping function IgFS produces a stable reference in coordinate system 50 that can be used to correct for drift and shifts in the detected position of electrical position sensor $44_1$ in coordinate system 50.

The above-described embodiment contemplates the use of a single magnetic position sensor $46_1$ as a positional reference for electrical position sensor $44_1$. If catheter 14 is equipped with multiple magnetic sensors $46_1$, $46_2$, however, or if multiple catheters having magnetic position sensors 46 are employed in body 12 at the same time, correction factors based on each magnetic position sensor 46 can be obtained and used to obtain the adjusted operation position for electrical position sensor $44_1$. Therefore, another embodiment of a method in accordance with the present teachings may recursively apply steps 82, 84, 86 (including substeps 88, 90) for each magnetic position sensor 46. Thus, the method may include the step of determining an operating position for another magnetic position sensor disposed proximate electrical position sensor $44_1$ such as magnetic position sensor $46_2$ on catheter 14 within coordinate system 52. The method may further include the step of applying mapping function IgFS to generate a mapped position for magnetic position sensor $46_2$ in coordinate system 50 responsive to the operating position of magnetic position sensor $46_2$. The method may continue with the step of determining an adjusted operating position for electrical position sensor $44_1$ in coordinate system 50 responsive to the mapped position of magnetic position sensor $46_2$. In particular, a difference may again be determined between the operating position for electrical position sensor $44_1$ in coordinate system 50 and the mapped position for magnetic position sensor $46_2$ in coordinate system 50:

$$\vec{\Delta}_2 = IgFS(\vec{g46_2}) - \vec{n44_1}$$

Thereafter, the operating position for electrical position sensor $44_1$ in coordinate system 50 may be modified by the difference to obtain the adjusted or corrected operating position of electrical position sensor $44_1$ in coordinate system 50:

$$\vec{n44}_{1corr} = \vec{n44}_1 + \vec{\Delta}_2$$

After determining an adjusted or corrected operating position for electrical position sensor $44_1$ in coordinate system 50 responsive to the mapped positions of each magnetic position sensor 46, the method may continue with the step 92 of determining a total adjusted operating position for electrical position sensor $44_1$ in coordinate system 50. In the case of a single magnetic sensor 46, the total adjusted operating position will simply be the same as the adjusted operating position obtained based on that magnetic sensor. In the case of multiple magnetic position sensors 46, the total adjusted operating position may be calculated in various ways. In one embodiment, step 92 includes a substep 94 of averaging the adjusted operating positions. In another embodiment, step 92 includes the substep 94 of weighting each of the adjusted operating positions responsive to actual distances of electrical position sensor $44_1$ relative to the magnetic position sensors $46_1$, $46_2$ such that, for example, the adjusted operating position obtained in response to magnetic position sensor $46_1$, which is closer to electrical position sensors $44_1$, is accorded more weight than the adjusted operating position obtained in response to magnetic position sensor $46_2$. In yet another embodiment, the adjusted operating positions are weighted based on the distance of the operating position for each magnetic position sensors $46_1$, $46_2$, from the planning positions measured earlier in order to account for potential decreases in accuracy in mapping functions gFS and IgFS as one moves further from the reference points used to construct the functions. The distance determination can be made in a variety of ways known in the art. In one embodiment, the magnetic space is divided into a grid of cells each of which contains one of the planning positions or is empty. Once an operating position for sensor $46_1$, $46_2$, is known, a corresponding cell can be identified and surrounding cells examined to identify the distance to the nearest planning position. In order to avoid abrupt changes or discontinuities, the weighting for adjusted operating positions based on sensors that are relatively far away from planning positions may be gradually adjusted (increased or decreased) over time instead of being simply proportional to distance. Thus, if a magnetic position sensor 46 moves abruptly, is removed from body 14 or is disabled in some way, its contribution to the total adjusted operating position is gradually adjusted rather than causing a sudden shift. In the case where the only or final magnetic sensor 46 becomes disabled or leaves the magnetic field, its last known operating position is retained for used in obtaining the adjusted or corrected operating position for electrical position sensor $44_1$ in coordinate system 50. If the sensor 46 becomes enabled or otherwise returns to the magnetic field, a gradual transition is made from the last known operating position to the current operating position.

The method may continue with the step 98 of applying mapping function gFS to generate a mapped position for electrical position sensor $44_1$ in coordinate system 52 responsive to the adjusted operating position $\vec{n44}_{1corr}$ for electrical position sensor $44_1$ in coordinate system 50:

$$\vec{g44}_1 = gFS(\vec{n44}_{1corr})$$

Finally, the method may also include the step 100 of displaying an image corresponding to electrical position sensor $44_1$ on display 22 responsive to the adjusted operating position $\vec{n44}_{1corr}$ by, for example, using the value acquired in step 94.

Figure 4:
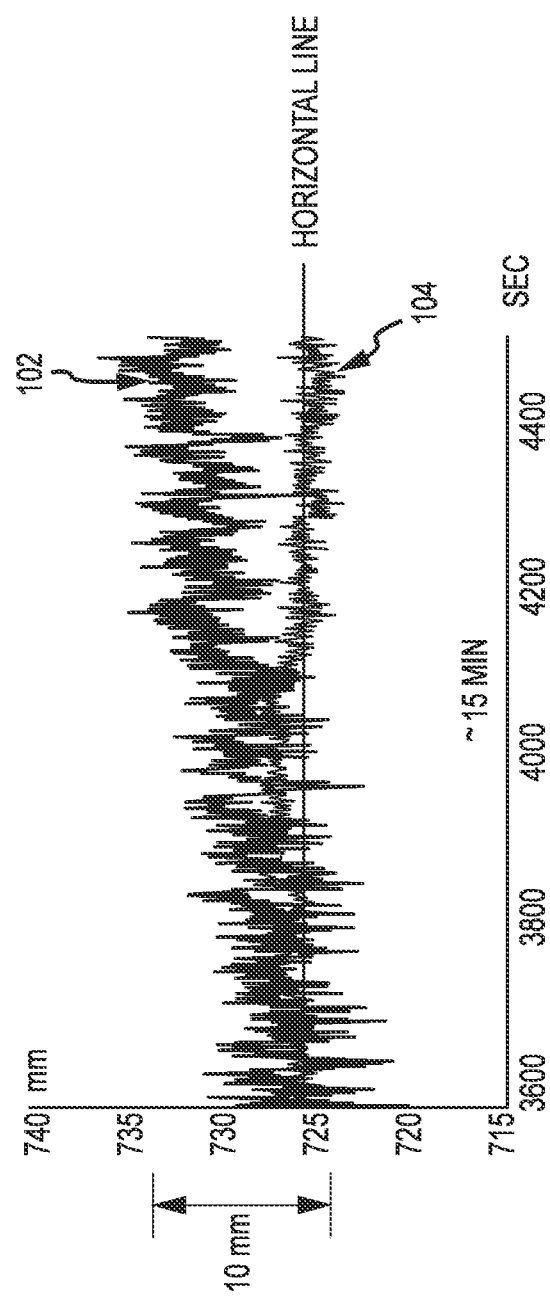
FIG. 4 is a graphical representation illustrating the detected position of an electrical position sensor on a medical device over time with and without use of a system and method in accordance with the present teachings.

Referring now to FIG. 4, the impact of the system 10 and method is illustrated. The system 10 and method were tested using position data obtained for electrical position sensors 44 and magnetic position sensors 46 using the systems made available under the trademark "ENSITE NAVX" by St. Jude Medical, Inc. and under the trademark "GMPS" by MediGuide, Ltd., respectively. FIG. 4 illustrates a trace 102 for the position of one electrical position sensor 44 along one axis disposed proximate a magnetic position sensor 46 as determined without use of the system and method. FIG. 4 further illustrates a trace 104 for the position of the same position sensor 44 adjusted or corrected using the system 10 and method described herein. As illustrated in FIG. 4, use of the system and method reduced the variability in the original trace 102 and removed much of the drift in the signal.

A system 10 and method for navigating a medical device within a body 12 in accordance with the present teachings enables consistent correction or errors in position measurements due to shift or drift in patient impedance levels. Further, the system 10 and method do not require the use of an additional reference catheter and the resulting increases in procedure time and risks.

Although several embodiments of this invention have been described above with a certain degree of particularity, those skilled in the art could make numerous alterations to the disclosed embodiments without departing from the scope of this invention. All directional references (e.g., upper, lower, upward, downward, left, right, leftward, rightward, top, bottom, above, below, vertical, horizontal, clockwise and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the invention as defined in the appended claims.

What is claimed is:

1. A system for navigating a medical device within a body, comprising:
   an electronic control unit configured to:
      determine an operating position for a first electrical position sensor on said medical device within a first coordinate system, said first coordinate system defined by an electric field based positioning system;
      determine an operating position for a first magnetic position sensor on said medical device within a second coordinate system, said second coordinate system defined by a magnetic field based positioning system, said first magnetic position sensor disposed proximate said first electrical position sensor;
      apply a first mapping function correlating said operating positions of said first electrical position sensor and said first magnetic position sensor, said first mapping function generating a mapped position for said first magnetic position sensor in said first coordinate system responsive to said operating position of said first magnetic position sensor in said second coordinate system wherein said first mapping function describes a three-dimensional input and a three-dimensional output that generates said mapped position;
      determine a first difference between said operating position for said first electrical position sensor and said mapped position for said first magnetic position sensor; and
      modify said operating position for said first electrical position sensor by said first difference to obtain a first adjusted operating position;
   wherein said electronic control unit is further configured to:
      determine a planning position for said first electrical position sensor within said first coordinate system;
      determine a planning position for said first magnetic position sensor within said second coordinate system;

compute said first mapping function responsive to said planning positions for said first electrical position sensor and said first magnetic position sensor; and, responsive to the first adjusted operating position, displaying on a graphical user interface the first adjusted operating position of the first electrical position sensor of the medical device.

2. The system of claim 1 wherein said electronic control unit is further configured to apply a second mapping function correlating said operating positions of said first electrical position sensor and said first magnetic position sensor, said second mapping function generating a mapped position for said first electrical position sensor in said second coordinate system responsive to said first adjusted operating position for said first electrical position sensor in said first coordinate system.

3. The system of claim 1 wherein said electronic control unit is further configured to:
  determine a virtual planning position for said first electrical position sensor within said first coordinate system, said virtual planning position located at a boundary in said first coordinate system; and,
  determine a virtual planning position for said first magnetic position sensor within said second coordinate system, said virtual planning position for said first magnetic sensor corresponding to said virtual planning position for said first electrical position sensor;
  wherein said first mapping function is computed responsive to said virtual planning positions for said first electrical position sensor and said first magnetic position sensor.

4. The system of claim 1 wherein said electronic control unit is further configured to compute a second mapping function responsive to said planning positions for said first electrical position sensor and said first magnetic position sensor, said second mapping function correlating said planning positions of said first electrical position sensor and said first magnetic position sensors, said second mapping function generating a mapped position for said first electrical position sensor in said second coordinate system responsive to said planning position of said first electrical position sensor in said first coordinate system.

5. The system of claim 1 wherein said electronic control unit is further configured to:
  determine a planning position for a second electrical position sensor on said medical device within said first coordinate system, said second electrical position sensor disposed proximate said first magnetic position sensor; and,
  average said planning positions of said first and second electrical position sensors before computing said first mapping function.

6. The system of claim 1 wherein said electronic control unit is further configured to:
  determine a planning position for one of a second electrical position sensor within said first coordinate system and a second magnetic position sensor within said second coordinate system;
  compare a distance between said planning position of said one position sensor and said planning position of a corresponding one of said first electrical position sensor and said first magnetic position sensor; and,
  discard said planning position for said one position sensor if said distance meets a predetermined characteristic relative to a predetermined threshold.

7. The system of claim 1 wherein said electronic control unit is further configured to:

determine an operating position for a second magnetic position sensor on said medical device within said second coordinate system, said second magnetic position sensor disposed proximate said first electrical position sensor;
  apply a second mapping function correlating said operating positions of said first electrical position sensor and said second magnetic position sensor, said second mapping function generating a mapped position for said second magnetic position sensor in said first coordinate system responsive to said operating position of said second magnetic position sensor in said second coordinate system;
  determine a second difference between said operating position for said first electrical position sensor and said mapped position for said second magnetic position sensor;
  modify said operating position for said first electrical position sensor by said second difference to obtain a second adjusted operating position; and
  determine a total adjusted operating position for said first electrical position sensor in said first coordinate system responsive to said first and second adjusted operating positions.

8. The system of claim 7 wherein said electronic control unit is further configured, in determining said total adjusted operating position, to average said first and second adjusted operating positions.

9. The system of claim 7 wherein said electronic control unit is further configured, in determining said total adjusted operating position, to weight each of said first and second adjusted operating positions responsive to actual distances of said first electrical position sensor relative to said first magnetic position sensor and said second magnetic position sensor.

10. The system of claim 1 wherein said electronic control unit is further configured to display an image corresponding to said first electrical position sensor on the display responsive to said first adjusted operating position.

11. A method for navigating a medical device within a body, comprising:
  determining, with a processor, an operating position for a first electrical position sensor on said medical device within a first coordinate system, said first coordinate system defined by an electric field based positioning system;
  determining, with the processor, an operating position for a first magnetic position sensor on said medical device within a second coordinate system, said second coordinate system defined by a magnetic field based positioning system, said first magnetic position sensor disposed proximate said first electrical position sensor;
  applying, with the processor, a first mapping function correlating said operating positions of said first electrical position sensor and said first magnetic position sensor, said first mapping function generating a mapped position for said first magnetic position sensor in said first coordinate system responsive to said operating position of said first magnetic position sensor in said second coordinate system, wherein said first mapping function describes a three-dimensional input and a three-dimensional output that generates said mapped position;
  determining, with the processor, a first difference between said operating position for said first electrical position sensor and said mapped position for said first magnetic position sensor;

modifying, with the processor, said operating position for said first electrical position sensor by said first difference to obtain a first adjusted operating position; and, responsive to the first adjusted operating position, displaying on a graphical user interface the first adjusted operating position of the first electrical position sensor of the medical device, further comprising:

determining a planning position for said first electrical position sensor within said first coordinate system;

determining a planning position for said first magnetic position sensor within said second coordinate system; and, computing said first mapping function responsive to said planning positions for said first electrical position sensor and said first magnetic position sensor.

12. The method of claim 11, further comprising:

applying, with the processor, a second mapping function correlating said operating positions of said first electrical position sensor and said first magnetic position sensor, said second mapping function generating a mapped position for said first electrical position sensor in said second coordinate system responsive to said first adjusted operating position for said first electrical position sensor in said first coordinate system.

13. The method of claim 11, further comprising:

determining a virtual planning position for said first electrical position sensor within said first coordinate system, said virtual planning position located at a boundary in said first coordinate system; and, determining a virtual planning position for said first magnetic position sensor within said second coordinate system, said virtual planning position for said first magnetic sensor corresponding to said virtual planning position for said first electrical position sensor;

wherein said first mapping function is computed responsive to said virtual planning positions for said first electrical position sensor and said first magnetic position sensor.

14. The method of claim 11, further comprising:

computing a second mapping function responsive to said planning positions for said first electrical position sensor and said first magnetic position sensor, said second mapping function correlating said planning positions of said first electrical position sensor and said first magnetic position sensors, said second mapping function generating a mapped position for said first electrical position sensor in said second coordinate system responsive to said planning position of said first electrical position sensor in said first coordinate system.

15. The method of claim 11, further comprising:

determining a planning position for a second electrical position sensor on said medical device within said first coordinate system, said second electrical position sensor disposed proximate said first magnetic position sensor; and, averaging said planning positions of said first and second electrical position sensors before computing said first mapping function.

16. The method of claim 11, further comprising:

determining a planning position for one of a second electrical position sensor within said first coordinate system and a second magnetic position sensor within said second coordinate system;

comparing a distance between said planning position of said one position sensor and said planning position of a corresponding one of said first electrical position sensor and said first magnetic position sensor; and, discarding said planning position for said one position sensor if said distance meets a predetermined characteristic relative to a predetermined threshold.

17. The method of claim 11, further comprising:

determining, with the processor, an operating position for a second magnetic position sensor on said medical device within said second coordinate system, said second magnetic position sensor disposed proximate said first electrical position sensor;

applying, with the processor, a second mapping function correlating said operating positions of said first electrical position sensor and said second magnetic position sensor, said second mapping function generating a mapped position for said second magnetic position sensor in said first coordinate system responsive to said operating position of said second magnetic position sensor in said second coordinate system;

determining, with the processor, a second difference between said operating position for said first electrical position sensor and said mapped position for said first magnetic position sensor;

modifying, with the processor, said operating position for said first electrical position sensor by said second difference to obtain a second adjusted operating position;

determining, with the processor, a total adjusted operating position for said first electrical position sensor in said first coordinate system responsive to said first and second adjusted operating positions.

18. The method of claim 17 wherein determining a total adjusted operating position includes the substep of averaging, with the processor, said first and second adjusted operating positions.

19. The method of claim 17 wherein determining a total adjusted operating position includes the substep of weighting, with the processor, each of said first and second adjusted operating positions responsive to actual distances of said first electrical position sensor relative to said first magnetic position sensor and said second magnetic position sensor.

20. The method of claim 11, further comprising displaying an image corresponding to said first electrical position sensor on the display responsive to said adjusted operating position.

* * * * *